(12) United States Patent
Wollenberg

(10) Patent No.: US 7,306,948 B2
(45) Date of Patent: Dec. 11, 2007

(54) HIGH THROUGHPUT SCREENING METHODS FOR LUBRICATING OIL COMPOSITIONS

(75) Inventor: Robert H. Wollenberg, Orinda, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 328 days.

(21) Appl. No.: 10/779,422

(22) Filed: Feb. 13, 2004

(65) Prior Publication Data

US 2005/0181512 A1    Aug. 18, 2005

(51) Int. Cl.
*G01N 33/26* (2006.01)

(52) U.S. Cl. .......................... 436/60; 436/164; 422/63; 422/67; 422/68.1; 422/82.05; 508/110; 435/DIG. 2; 435/DIG. 9

(58) Field of Classification Search ................ 436/55, 436/60, 164, 165; 422/62, 63, 67, 68.1, 82.05, 422/82.09; 252/408.1; 508/110; 435/DIG. 1, 435/DIG. 2, DIG. 9, DIG. 22, DIG. 29, DIG. 45, 435/DIG. 46, DIG. 49
See application file for complete search history.

(56) References Cited

U.S. PATENT DOCUMENTS

| | | | |
|---|---|---|---|
| 5,715,046 A * | 2/1998 | Tolvanen et al. | ............. 356/70 |
| 5,959,297 A | 9/1999 | Weinberg et al. | |
| 5,985,356 A | 11/1999 | Schultz et al. | |
| 5,993,662 A * | 11/1999 | Garr et al. | ................... 210/656 |
| 6,004,617 A | 12/1999 | Schultz et al. | |
| 6,030,917 A | 2/2000 | Weinberg et al. | |
| 6,034,775 A | 3/2000 | McFarland et al. | |
| 6,045,671 A | 4/2000 | Wu et al. | |
| 6,087,181 A | 7/2000 | Cong | |
| 6,149,882 A | 11/2000 | Guan et al. | |
| 6,157,449 A | 12/2000 | Hajduk | |
| 6,175,409 B1 | 1/2001 | Nielsen et al. | |
| 6,182,499 B1 | 2/2001 | McFarland et al. | |
| 6,187,164 B1 | 2/2001 | Warren et al. | |
| 6,248,540 B1 | 6/2001 | Weinberg et al. | |
| 6,260,407 B1 | 7/2001 | Petro et al. | |
| 6,265,226 B1 | 7/2001 | Petro et al. | |
| 6,296,771 B1 | 10/2001 | Miroslav | |
| 6,326,090 B1 | 12/2001 | Schultz et al. | |
| 6,336,353 B2 | 1/2002 | Matsiev et al. | |
| 6,345,528 B2 | 2/2002 | Petro et al. | |
| 6,346,290 B1 | 2/2002 | Schultz et al. | |
| 6,371,640 B1 | 4/2002 | Hajduk et al. | |
| 6,373,570 B1 | 4/2002 | McFarland et al. | |

(Continued)

FOREIGN PATENT DOCUMENTS

EP        1233361      *   8/2002

(Continued)

*Primary Examiner*—Maureen M. Wallenhorst
(74) *Attorney, Agent, or Firm*—Claude J. Caroli; M. Carmen & Associates, PLLC

(57) ABSTRACT

Method for determining deposit formation tendencies for a plurality of fluid samples of different compositions is provided. Each sample includes one or more lubricating oil compositions containing at least one or more base oils of lubricating viscosity and one or more lubricating oil additives. The methods can advantageously be optimized using combinatorial chemistry, in which a database of combinations of lubricating oil compositions are generated. As market conditions vary and/or product requirements or customer specifications change, conditions suitable for forming desired products can be identified with little or no downtime.

23 Claims, 5 Drawing Sheets

U.S. PATENT DOCUMENTS

| | | |
|---|---|---|
| 6,393,895 B1 | 5/2002 | Matsiev et al. |
| 6,393,898 B1 | 5/2002 | Hajduk et al. |
| 6,395,552 B1 | 5/2002 | Borade et al. |
| 6,401,519 B1 | 6/2002 | McFarland et al. |
| 6,406,632 B1 | 6/2002 | Safir et al. |
| 6,410,331 B1 | 6/2002 | Schultz et al. |
| 6,419,881 B1 | 7/2002 | Weinberg et al. |
| 6,420,179 B1 | 7/2002 | Schultz et al. |
| 6,436,292 B1 | 8/2002 | Petro |
| 6,438,497 B1 | 8/2002 | Mansky et al. |
| 6,440,745 B1 | 8/2002 | Weinberg et al. |
| 6,441,901 B2 | 8/2002 | McFarland et al. |
| 6,461,515 B1 | 10/2002 | Safir et al. |
| 6,468,806 B1 | 10/2002 | McFarland et al. |
| 6,475,391 B2 | 11/2002 | Safir et al. |
| 6,484,567 B1 | 11/2002 | Hajduk et al. |
| 6,491,816 B2 | 12/2002 | Petro |
| 6,508,984 B1 | 1/2003 | Turner et al. |
| 6,519,032 B1 | 2/2003 | Kuebler et al. |
| 6,528,026 B2 | 3/2003 | Hajduk et al. |
| 6,535,284 B1 | 3/2003 | Hajduk et al. |
| 6,535,824 B1 | 3/2003 | Mansky et al. |
| 6,536,944 B1 | 3/2003 | Archibald et al. |
| 6,541,271 B1 | 4/2003 | McFarland et al. |
| 6,553,318 B2 | 4/2003 | Mansky |
| 6,576,906 B1 | 6/2003 | Archibald et al. |
| 6,577,392 B1 | 6/2003 | Nielsen et al. |
| 6,582,116 B2 | 6/2003 | Nielsen |
| 6,605,473 B1 | 8/2003 | Hajduk et al. |
| 6,644,101 B2 | 11/2003 | Hajduk et al. |
| 6,649,413 B1 | 11/2003 | Schultz et al. |
| 6,650,102 B2 | 11/2003 | Hajduk et al. |
| 6,653,138 B1 | 11/2003 | Turner et al. |
| 6,655,194 B1 | 12/2003 | Hajduk et al. |
| 6,658,429 B2 | 12/2003 | Dorsett, Jr. |
| 6,664,067 B1 | 12/2003 | Hajduk et al. |
| 6,668,622 B2 | 12/2003 | Hajduk et al. |
| 6,670,298 B1 | 12/2003 | Weinberg et al. |
| 6,679,130 B2 | 1/2004 | Hajduk et al. |
| 6,681,618 B2 | 1/2004 | Hajduk et al. |
| 6,686,205 B1 | 2/2004 | Schultz et al. |
| 6,690,179 B2 | 2/2004 | Hajduk et al. |
| 2002/0023507 A1 | 2/2002 | Hajduk et al. |
| 2002/0028456 A1 | 3/2002 | Mansky et al. |
| 2002/0029621 A1 | 3/2002 | Hajduk et al. |
| 2002/0032531 A1 | 3/2002 | Mansky et al. |
| 2002/0098332 A1 | 7/2002 | Warren et al. |
| 2002/0148282 A1 | 10/2002 | Hajduk et al. |
| 2002/0155036 A1 | 10/2002 | Hajduk et al. |
| 2002/0164275 A1 | 11/2002 | Wheeler et al. |
| 2003/0007152 A1 | 1/2003 | McFarland et al. |
| 2003/0032198 A1 | 2/2003 | Lugmair et al. |
| 2003/0032205 A1 | 2/2003 | McFarland et al. |
| 2003/0037601 A1 | 2/2003 | Mansky et al. |
| 2003/0037620 A1 | 2/2003 | Mansky |
| 2003/0041653 A1 | 3/2003 | Matsiev et al. |
| 2003/0041671 A1 | 3/2003 | Hajduk et al. |
| 2003/0041672 A1 | 3/2003 | Hajduk et al. |
| 2003/0041676 A1 | 3/2003 | Hajduk et al. |
| 2003/0054704 A1 | 3/2003 | Mansky |
| 2003/0055587 A1 | 3/2003 | Wang et al. |
| 2003/0056576 A1 | 3/2003 | Mansky |
| 2003/0068829 A1 | 4/2003 | Giaquinta et al. |
| 2003/0097871 A1 | 5/2003 | Mansky |
| 2003/0100119 A1 | 5/2003 | Weinberg et al. |
| 2003/0127776 A1 | 7/2003 | Carlson et al. |
| 2003/0133113 A1 | 7/2003 | Hajduk et al. |
| 2003/0138025 A1 | 7/2003 | Archibald et al. |
| 2003/0141613 A1 | 7/2003 | Hajduk et al. |
| 2003/0142309 A1 | 7/2003 | Kuebler et al. |
| 2003/0157721 A1 | 8/2003 | Turner et al. |
| 2003/0161763 A1 | 8/2003 | Erden et al. |
| 2003/0169638 A1 | 9/2003 | Nielsen |
| 2003/0171226 A1* | 9/2003 | Gatto ........................ 508/362 |
| 2003/0190260 A1 | 10/2003 | Wheeler et al. |
| 2003/0203500 A1 | 10/2003 | Carlson et al. |
| 2003/0211016 A1 | 11/2003 | Dales et al. |
| 2003/0218467 A1 | 11/2003 | Carlson et al. |
| 2003/0219906 A1 | 11/2003 | Giaquinta et al. |
| 2004/0123650 A1* | 7/2004 | Kolosov et al. ........... 73/54.28 |
| 2005/0095716 A1* | 5/2005 | Wollenberg et al. .......... 436/60 |
| 2005/0095717 A1* | 5/2005 | Wollenberg et al. .......... 436/60 |
| 2005/0182572 A1* | 8/2005 | Wollenberg ................. 702/22 |

FOREIGN PATENT DOCUMENTS

| | | |
|---|---|---|
| WO | WO 02/07870 | 1/2002 |

* cited by examiner

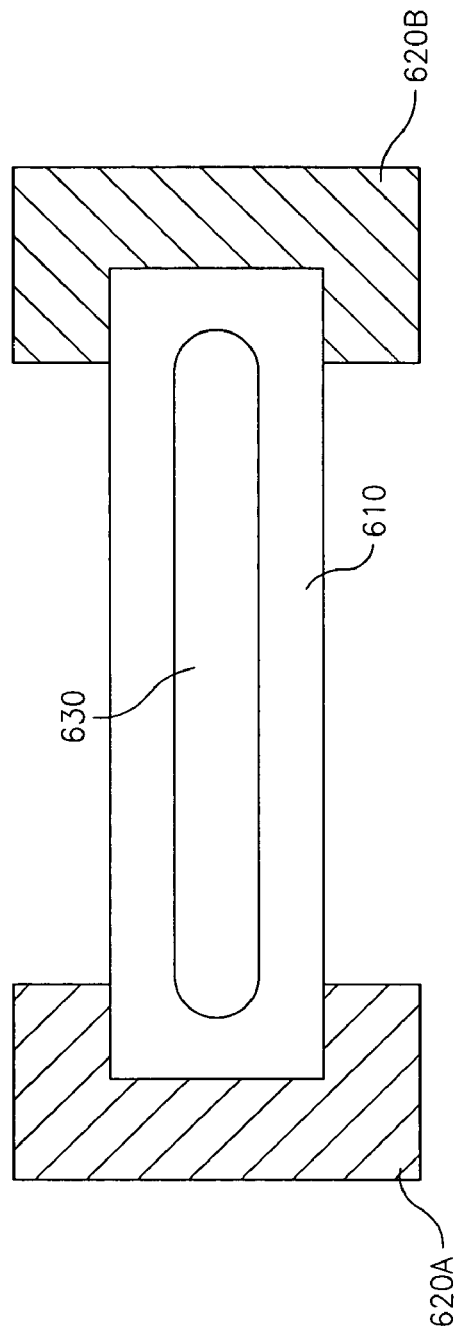
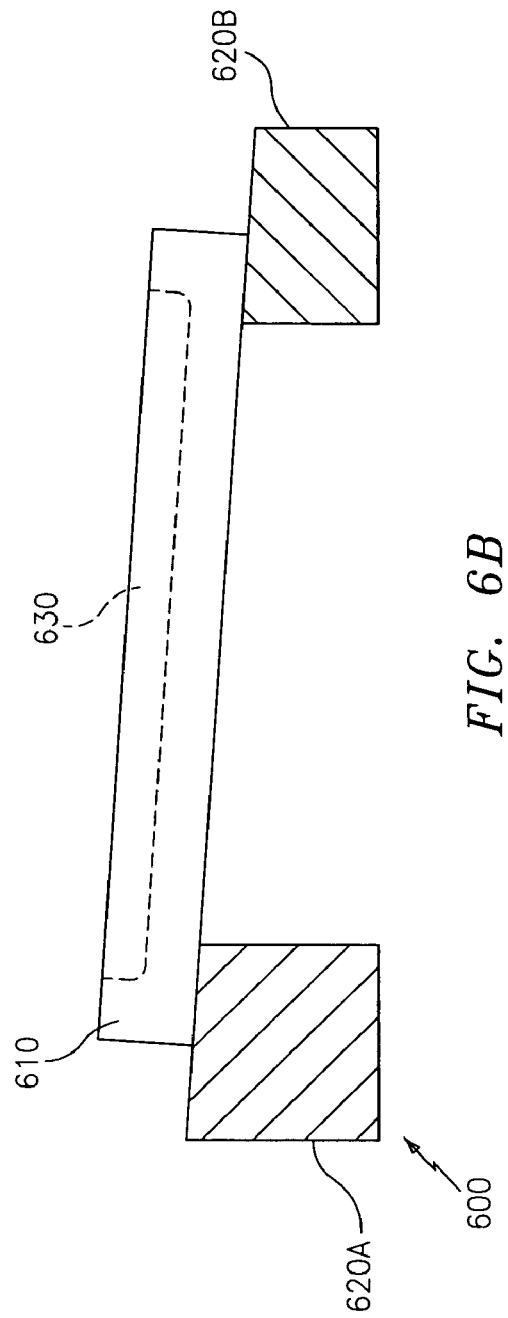
FIG. 6A
FIG. 6B

HIGH THROUGHPUT SCREENING METHODS FOR LUBRICATING OIL COMPOSITIONS

BACKGROUND OF THE INVENTION

1. Technical Field

The present invention relates generally to methods for high throughput screening of lubricating oil compositions.

2. Description of the Related Art

The use of a combinatorial approach for materials synthesis is a relatively new area of research aimed at using rapid synthesis and screening methods to build libraries of polymeric, inorganic or solid state materials. For example, advances in reactor technology have empowered chemists and engineers to rapidly produce large libraries of discrete organic molecules in the pursuit of new drug discovery, which have led to the development of a growing branch of research called combinatorial chemistry. Combinatorial chemistry generally refers to methods and materials for creating collections of diverse materials or compounds—commonly known as libraries—and to techniques and instruments for evaluating or screening libraries for desirable properties.

Presently, research in the lubricant industry involves individually forming candidate lubricating oil compositions and then performing a macro-scale analysis of the candidate compositions by employing a large amount of the candidate to be tested. Additionally, the methods employed for testing each candidate composition require manual operation. This, in turn, significantly reduces the number of compositions that can be tested and identified as leading compositions.

Drawbacks associated with conventional screening procedures can be seen as follows. For example, governmental and automotive industry pressure towards reducing the phosphorous and sulfur content of lubricating oil compositions used as, for example, passenger car and heavy duty diesel engine oils, is leading to new research to identify oil compositions which can satisfy certain tests such as, for example, oxidation, wear and compatibility tests, while containing low levels of phosphorous and sulfur. In this context, United States Military Standards MIL-L-46152E and the ILSAC Standards defined by the Japanese and United States Automobile Industry Association at present require the phosphorous content of engine oils to be at or below 0.10 wt. % with future phosphorous content being proposed to even lower levels, e.g., 0.08 wt. % by June, 2004 and below 0.05 wt. % by January, 2006. Also, at present, there is no industry standard requirement for sulfur content in engine oils, but it has been proposed that the sulfur content be below 0.3 wt. % to meet June, 2007 requirements for emissions. Thus, it would be desirable to decrease the amount of phosphorous and sulfur in lubricating oils still further, thereby meeting future industry standard proposed phosphorous and sulfur contents in the engine oil while still retaining the oxidation or corrosion inhibiting properties and antiwear properties of the higher phosphorous and sulfur content engine oils. In order to accomplish this, a large number of proposed lubricating oil compositions must be tested to determine which compositions may be useful.

Additionally, similar changes in specifications and changing customer needs also drive reformulation efforts in other lubricant applications such as, for example, transmission fluids, hydraulic fluids, gear oils, marine cylinder oils, compressor oils, refrigeration lubricants and the like.

However, as stated above, present research in the lubricant industry does not allow for reformulation to occur in an expeditious manner. As such, there exists a need in the art for a more efficient, economical and systematic approach for the preparation of lubricating oil compositions and screening of such compositions. For example, many lubricating oil compositions have deposit forming tendencies. Generally, deposit formation on hot and cold components of the engine includes the formation of gummy layers (of brown to black color) or harder deposits which are primarily carbon based deposits. These deposits impair the function of individual components such as, for example, free movement of the piston rings, constriction of air-conveying components of the turbocharger, etc. Consequently, serious engine damage or power loss is suffered in addition to an increase in exhaust-gas emissions. Furthermore, a spongy deposit layer forms preferentially on the horizontal surfaces of the oil space, and in the extreme case may also clog oil filters and oil ducts of the engine, potentially leading to engine damage.

Deposit formation also occurs when, for example, internal combustion engines of automobiles or trucks are subjected to a demanding environment during use. The environment results in the oil suffering oxidation which is catalyzed by the presence of impurity species in the oil such as, for example, iron compounds, and is also promoted by the elevated temperatures experienced by the oil during use. The catalyzed oxidation of the oil contributes to the formation of corrosive oxidation products and sludge in the oil but can also cause the viscosity of the oil to increase or even solidify.

Accordingly, it would be desirable to rapidly screen a plurality of sample candidate lubricating oil compositions for deposit formation tendencies utilizing small amounts of each sample. In this manner, a high throughput preparation and screening of a vast number of diverse compositions can be achieved to identify which additives and/or compositions have reduced deposit formation tendencies.

SUMMARY OF THE INVENTION

A high throughput screening method for determining deposit formation tendencies of lubricating oil compositions is provided herein. In accordance with one embodiment of the present invention, a high throughput method for screening lubricating oil compositions, under program control, is provided comprising the steps of (a) providing a plurality of different lubricating oil composition samples, each sample comprising (i) a major amount of at least one base oil of lubricating viscosity and (ii) a minor amount of at least one lubricating oil additive; (b) measuring the deposit formation of each sample to provide deposit formation data for each sample; and, (c) outputting the results of step (b).

In a second embodiment of the present invention, a system for determining deposit formation tendencies of lubricating oil composition samples is provided comprising:

(a) a plurality of test receptacles, each receptacle containing a different lubricating oil composition sample comprising (i) a major amount of at least one base oil of lubricating viscosity and (ii) a minor amount of at least one lubricating oil additive;

(b) receptacle moving means for individually positioning the test receptacles in a testing station for measurement of deposit formation of the respective sample;

(c) means for measuring the deposit formation of each respective sample in the testing station to obtain deposit formation data associated with the sample and for transferring the deposit formation data to a computer controller.

The methods and systems of the present invention advantageously permit the screening of many different composition samples in an efficient manner to determine deposit formation tendencies of the samples, e.g., how fast deposits form, at what temperatures do deposits form and the weight of the deposits.

BRIEF DESCRIPTION OF THE DRAWINGS

Various embodiments are described below with reference to the drawings wherein:

FIG. 6A is a schematic diagram of a top view of a system for measuring deposit formation tendencies of a plurality of samples of lubricating oil compositions employing a temperature gradient method; and, FIG. 6B is a schematic diagram of a side view of the system of FIG. 6A.

DETAILED DESCRIPTION OF THE PREFERRED EMBODIMENT(S)

Figure 1:
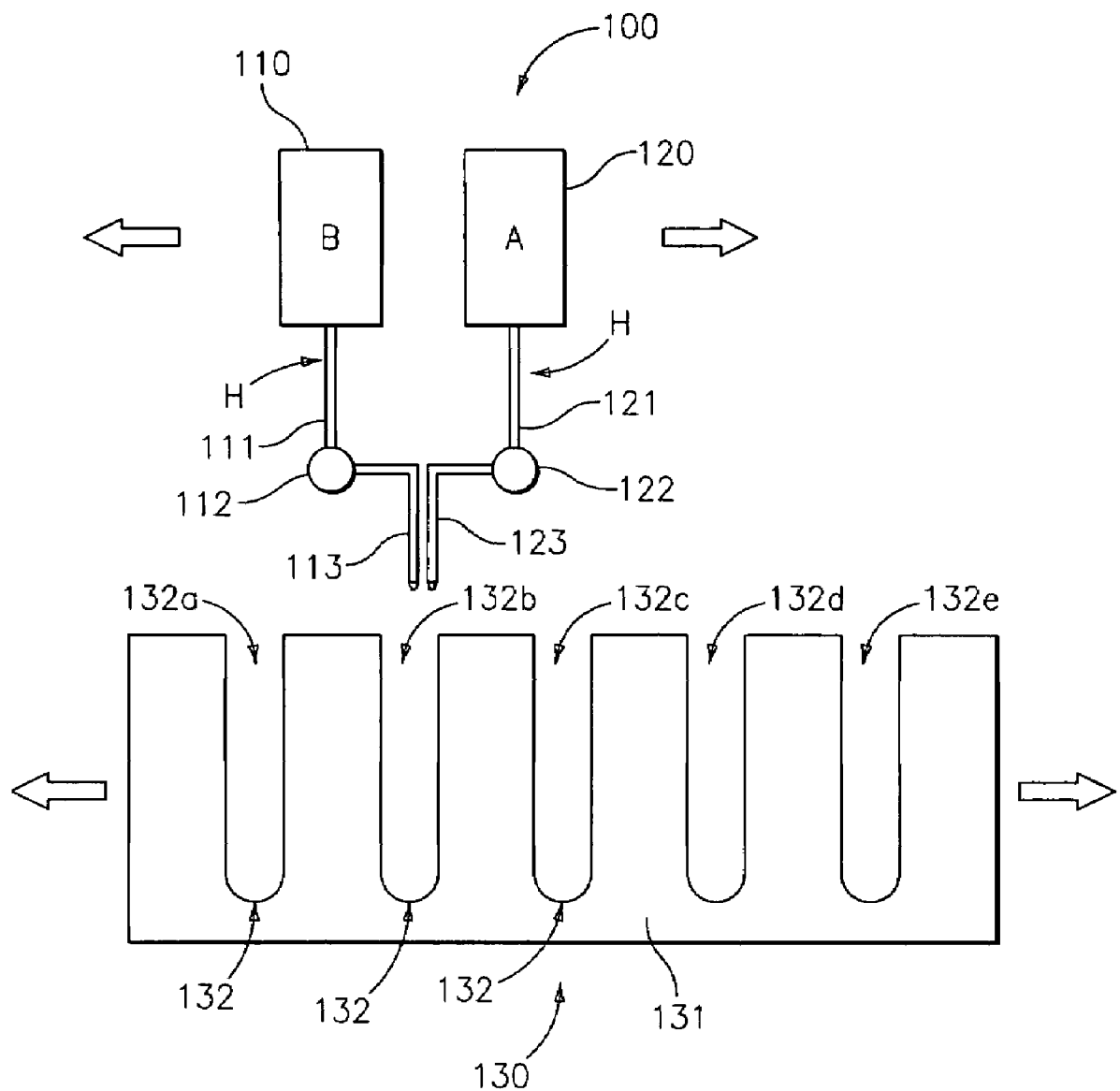
FIG. 1 is a schematic diagram of a system for preparing a plurality of different lubricating oil compositions.

The present invention is directed to a high throughput screening method for determining deposit formation tendencies of lubricating oil compositions. The expression "high throughput" as used herein shall be understood to mean that a relatively large number of different lubricating oil compositions can be rapidly prepared and analyzed. In a first step of one embodiment of the screening method of the present invention, at least one lubricating oil composition is introduced in a plurality of respective test receptacles so that each receptacle contains a different lubricating oil composition having a different composition depending upon the percentage amounts and/or types of the at least one base oil and/or at least one additive combined in each receptacle.

Data regarding the composition of each sample are stored in a data library. Adding the information related to the deposit formation data of each of the stored compositions substantially facilitates the selection of candidate compositions capable of successfully carrying out the deposit formation tests under the desired operating conditions or statutory requirements. Accordingly, storing this information in the combinatorial library not only allows for a rapid selection of multiple lubricating oil compositions in response to new requirements for a given test, but also becomes another piece of information in addition to, for example, storage stability, oxidation stability, wear stability, dispersancy data, elastomer compatibility, etc., of the cataloged compositions. This information may also allow for calculating necessary changes of the additives at the least cost. The procedure is advantageously accomplished under program control and automatically controlled by, for example, a microprocessor or other computer control device. The expression "program control" as used herein shall be understood to mean the equipment used herein in providing the plurality of lubricating oil compositions is automated and controlled by a microprocessor or other computer control device.

The lubricating oil compositions for use in the high throughput screening method of this invention include at least one base oil of lubricating viscosity and at least one lubricating oil additive. Generally, the lubricating oil compositions for use in the high throughput screening method of this invention include a minor amount of at least one of the foregoing lubricating oil additives together with a major amount of at least one base oil of lubricating viscosity, e.g., an amount of greater than 50 wt. %, preferably greater than about 70 wt. %, more preferably from about 80 to about 99.5 wt. % and most preferably from about 85 to about 98 wt. %, based on the total weight of the composition.

The expression "base oil" as used herein shall be understood to mean a base stock or blend of base stocks which is a lubricant component that is produced by a single manufacturer to the same specifications (independent of feed source or manufacturer's location): that meets the same manufacturer's specification; and that is identified by a unique formula, product identification number, or both. The base oil for use herein can be any presently known or later-discovered base oil of lubricating viscosity used in formulating lubricating oil compositions for any and all such applications, e.g., engine oils, marine cylinder oils, natural gas engine oils, railroad oils, two-cycle engine oils, tractor oils, heavy duty diesel engine oils, truck oils and functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C.) Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fisher-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a moleclur wieght of 1,000-1,500, etc.) or mono- and polycarboxylic esters thereof such as, for example, the acetic esters, mixed $C_3$-$C_8$ fatty acid esters, or the $C_{13}$oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The second component of the lubricating oil compositions herein is at least one lubricating oil additive. The lubricating oil additives for use herein can be any presently known or later-discovered additive used in formulating lubricating oil compositions. The lubricating oil additives for use herein include, but are not limited to, antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. Greases will require the addition of appropriate thickeners. A variety of the additives are known and commercially available. These additives, or their analogous compounds, can be employed for the preparation of the various lubricating oil compositions herein. Preferably, the at least one additive is an antioxidant, detergent, ashless dispersant or mixtures thereof.

Alternatively, the lubricating oil additive(s) can further contain a diluent oil to form an additive concentrate. These concentrates usually include at least from about 98 wt. % to about 10 wt. %, preferably from about 98 wt. % to about 25 wt. % and most preferably from about 97 wt. % to about 50 wt. % of a diluent oil and from about 2 wt. % to about 90 wt. %, preferably from about 2 wt. % to about 75 wt. % and most preferably from about 3 wt. % to about 50 wt. %, of the foregoing additive(s). Suitable diluents for the concentrates include any inert diluent, preferably an oil of lubricating viscosity such as, for example, a base oil as described hereinbelow, so that the concentrate may be readily mixed with lubricating oils to prepare lubricating oil compositions. Suitable lubricating oils that may be used as diluents can be any oil of lubricating viscosity.

Examples of antioxidants include, but are not limited to, aminic types, phenolics, sterically hindered phenols, secondary aromatic amine antioxidants, sulfurized phenolic antioxidants, oil-soluble copper compounds, phosphorus-containing antioxidants, organic sulfides, disulfides and polysulfides and the like.

Examples of sterically hindered phenolic antioxidants include, but are not limited to, ortho-alkylated phenolic compounds such as 2,6-di-tertbutylphenol, 4-methyl-2,6-di-tertbutylphenol, 2,4,6-tri-tertbutylphenol, 2-tert-butylphenol, 2,6-diisopropylphenol, 2-methyl-6-tert-butylphenol, 2,4-dimethyl-6-tert-butylphenol, 4-(N,N-dimethylaminomethyl)-2, 6-di-tertbutyl phenol, 4-ethyl-2,6-di-tertbutylphenol, 2-methyl-6-styrylphenol, 2,6-distyryl-4-nonylphenol, and their analogs and homologs. Mixtures of two or more such mononuclear phenolic compounds are also suitable.

Examples of other phenol antioxidants for use in the lubricating oil compositions of the present invention include, but are not limited to, one or more methylene bridged alkylphenols, one or more sterically-hindered unbridged phenolic compounds and mixtures thereof Examples of methylene-bridged compounds include, but are not limited to, 4,4'-methylenebis(6-tert-butyl o-cresol), 4,4'-methylenebis(2-tert-amyl-o-cresol), 2,2'-methylenebis(4-methyl-6-tert-butylphenol), 4,4'-methylene-bis(2,6-di-tert-butylphenol), and the like. Particularly preferred are mixtures of methylene-bridged alkylphenols such as those described in U.S. Pat. No. 3,211,652, the contents of which are incorporated by reference herein.

Amine antioxidants can also be used in the lubricating oil compositions of this invention. Examples include, but are not limited to, oil-soluble aromatic secondary amines, aromatic secondary polyamines and the like and combinations thereof with aromatic secondary amines being preferred. Examples of aromatic secondary monoamines include diphenylamine, alkyl diphenylamines containing 1 or 2 alkyl substituents each having up to about 16 carbon atoms, phenyl-alpha-naphtylamine, phenyl-beta-naphtylamine, alkyl- or aralkylsubstituted phenyl-alpha-naphtylamine containing at least one or two alkyl or aralkyl groups each having up to about 16 carbon atoms, alkyl- or aralkyl-substituted phenyl-beta-naphthylamine containing at least one or two alkyl or aralkyl groups each having up to about 16 carbon atoms, and the like.

A preferred type of aromatic amine antioxidant is an alkylated diphenylamine of the general formula

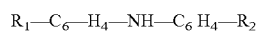

wherein $R_1$ is an alkyl group (preferably a branched alkyl group) having 6 to 12 carbon atoms and preferably 8 or 9 carbon atoms; and $R_2$ is a hydrogen atom or an alkyl group (preferably a branched alkyl group) having 6 to 12 carbon atoms and preferably 8 or 9 carbon atoms. Most preferably, $R_1$ and $R_2$ are the same. One such preferred compound is available commercially as Naugalube 438L, a material which is understood to be predominately a 4,4'-dinonyl-diphenylamine, i.e., bis(4-nonylphenylamine), wherein the nonyl groups are branched.

Another antioxidant for use in the lubricating oil compositions of this invention is comprised of one or more liquid, partially sulfurized phenolic compounds such as those prepared by reacting sulfur monochloride with a liquid mixture of phenols wherein at least about 50 weight percent of the mixture of phenols is composed of one or more reactive, hindered phenols and in proportions to provide from about 0.3 to about 0.7 gram atoms of sulfur monochloride per mole of reactive, hindered phenol so as to produce a liquid product. Typical phenol mixtures useful in making such liquid product compositions include a mixture containing by weight about 75% of 2,6-di-tert-butylphenol, about 10% of 2-tert-butylphenol, about 13% of 2,4,6-tri-tertbutylphenol, and about 2% of 2,4-di-tertbutylphenol. The reaction is exothermic and is preferably kept within the range of about 15° C. to about 70° C., most preferably between about 40° C. to about 60° C.

Mixtures of different antioxidants can also be used in the lubricating oil compositions of the present invention. One suitable mixture is comprised of a combination of (i) an oil-soluble mixture of at least three different sterically-hindered tertiary butylated monohydric phenols which is in the liquid state at 25° C., (ii) an oil-soluble mixture of at least three different sterically-hindered tertiary butylated methylene-bridged polyphenols, and (iii) at least one bis(4-alkylphenyl) amine wherein the alkyl group is a branched alkyl group having 8 to 12 carbon atoms, the proportions of (i), (ii) and (iii) on a weight basis falling in the range of about 3.5 to about 5.0 parts of component (i) and about 0.9 to about 1.2 parts of component (ii) per part by weight of component (iii). Examples of such antioxidants discussion above are disclosed in U.S. Pat. No. 5,328,619, the contents of which are incorporated by reference herein. Other useful antioxidants are those disclosed in U.S. Pat. No. 4,031,023, the contents of which are incorporated by reference herein.

Examples of antiwear agents include, but are not limited to, zinc dialkyldithiophosphates and zinc diaryldithiophosphates, e.g., those described in an article by Born et al. entitled "Relationship between Chemical Structure and Effectiveness of Some Metallic Dialkyl- and Diaryl-dithiophosphates in Different Lubricated Mechanisms", appearing in Lubrication Science 4-2 Jan. 1992, see for example pages 97-100; aryl phosphates and phosphites, sulfur-containing esters, phosphosulfur compounds, metal or ash-free dithiocarbamates, xanthates, alkyl sulfides and the like and mixtures thereof.

Examples of detergents include, but are not limited to, overbased or neutral detergents such as sulfonate detergents, e.g., those made from alkyl benzene and fuming sulfuric acid, Group II metal overbased sulfurized alkylphenols, etc.;

phenates (high overbased or low overbased); high overbased phenate stearates; phenolates; salicylates; phosphonates; thiophosphonates; ionic surfactants and the like and mixtures thereof. Low overbased metal sulfonates typically have a total base number (TBN) of from about 0 to about 30 and preferably from about 10 to about 25. Low overbased metal sulfonates and neutral metal sulfonates are well known in the art.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine, e.g., those disclosed in U.S. Ser. No. 10/402,170, filed Mar. 28, 2003, the contents of which are incorporated by reference herein, and the like and mixtures thereof.

Examples of antifoaming agents include, but are not limited to, polymers of alkyl methacrylate; polymers of dimethylsilicone and the like and mixtures thereof.

Examples of ashless dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonamides, thiophosphonamides and phosphoramides; thiazoles, e.g., 2,5-dimercapto-1,3,4-thiadiazoles, mercaptobenzothiazoles and derivatives thereof; triazoles, e.g., alkyltriazoles and benzotriazoles; copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof.

The polyalkylene succinic anhydride dispersant is preferably a polyisobutenyl succinic anhydride (PIBSA). The number average molecular weight of the polyalkylene tail in the polyalkylene succinic anhydrides used herein will be at least 350, preferably from about to about 750 to about 3000 and most preferably from about 900 to about 1100. Examples of suitable polyalkylene succinic anhydrides for use herein are thermal PIBSA (polyisobutenyl succinic anhydride) described in U.S. Pat. No. 3,361,673; chlorinated PIBSA described in U.S. Pat. No. 3,172,892; a mixture of thermal and chlorinated PIBSA described in U.S. Pat. No. 3,912,764; high succinic ratio PIBSA described in U.S. Pat. No. 4,234,435; polyPIBSA described in U.S. Pat. Nos. 5,112,507 and 5,175,225; high succinic ratio polyPIBSA described in U.S. Pat. Nos. 5,565,528 and 5,616,668; free radical PIBSA described in U.S. Pat. Nos. 5,286,799, 5,319,030 and 5,625,004; PIBSA made from high methylvinylidene polybutene described in U.S. Pat. Nos. 4,152,499, 5,137,978 and 5,137,980; high succinic ratio PIBSA made from high methylvinylidene polybutene described in European Pat. Application Publication No. EP 355 895; terpolymer PIBSA described in U.S. Pat. No. 5,792,729, sulfonic acid PIBSA described in U.S. Pat. No. 5,777,025 and European Pat. Application Publication No. EP 542 380; and purified PIBSA described in U.S. Pat. No. 5,523,417 and European Pat. Application Publication No. EP 602 863, the contents of each of these references being incorporated herein by reference.

Non-nitrogen containing derivatives of polyalkylene succinic anhydrides include, but are not limited to, succinic acids, Group I and/or Group II mono- or di-metal salts of succinic acids, succinate esters formed by the reaction of a polyalkylene succinic anhydride, acid chloride, or other derivatives with an alcohol (e.g., $HOR^1$ wherein $R^1$ is an alkyl group of from 1 to 10 carbon atoms) and the like and mixtures thereof.

If desired, the foregoing polyalkylene succinic anhydrides and/or non-nitrogen-containing derivatives thereof can be post-treated with a wide variety of post-treating reagents. For example, the foregoing polyalkylene succinic anhydride and/or derivatives thereof can be reacted with boron or a cyclic carbonate, e.g., ethylene carbonate, to provide borate post-treated and ethylene carbonate post-treated products.

The basic nitrogen compound for use herein must contain basic nitrogen as measured, for example, by ASTM D664 test or D2896. The basic nitrogen compounds are selected from the group consisting of succinimides, polysuccinimides, carboxylic acid amides, hydrocarbyl monoamines, hydrocarbon polyamines, Mannich bases, phosphoramides, thiophosphoramides, phosphonamides, dispersant viscosity index improvers, and mixtures thereof. These basic nitrogen-containing compounds are described below (keeping in mind the reservation that each must have at least one basic nitrogen). Any of the nitrogen-containing compositions may be post-treated with, e.g., boron or ethylene carbonate, using procedures well known in the art so long as the compositions continue to contain basic nitrogen.

The succinimides and polysuccinimides that can be used herein are disclosed in numerous references and are well known in the art. Certain fundamental types of succinimides and the related materials encompassed by the term of art "succinimide" are taught in U.S. Pat. Nos. 3,219,666; 3,172,892; and 3,272,746, the contents of which are incorporated by reference herein. The term "succinimide" is understood in the art to include many of the amide, imide, and amidine species which may also be formed. The predominant product, however, is a succinimide and this term has been generally accepted as meaning the product of a reaction of an alkenyl substituted succinic acid or anhydride with a nitrogen-containing compound. Preferred succinimides, because of their commercial availability, are those succinimides prepared from a hydrocarbyl succinic anhydride, wherein the hydrocarbyl group contains from about 24 to about 350 carbon atoms, and an ethylene amine, said ethylene amines being especially characterized by ethylene diamine, diethylene triamine, triethylene tetramine, tetraethylene pentamine, and higher molecular weight polyethylene amines. Particularly preferred are those succinimides prepared from polyisobutenyl succinic anhydride of 70 to 128 carbon atoms and tetraethylene pentamine or higher molecular weight polyethylene amines or mixtures of polyethylene amines such that the average molecular weight of the mixture is about 205 Daltons.

Also included within the term "succinimide" are the co-oligomers of a hydrocarbyl succinic acid or anhydride and a polysecondary amine containing at least one tertiary amino nitrogen in addition to two or more secondary amino groups. Ordinarily, this composition has between 1,500 and 50,000 average molecular weight. A typical compound would be that prepared by reacting polyisobutenyl succinic anhydride and ethylene dipiperazine.

Carboxylic acid amide compounds are also useful nitrogen-containing compounds for preparing the colloidal suspensions of this invention. Typical of such compounds are those disclosed in U.S. Pat. No. 3,405,064, the contents of which are incorporated by reference herein. These compounds are ordinarily prepared by reacting a carboxylic acid or anhydride or ester thereof, having at least 12 to about 350 aliphatic carbon atoms in the principal aliphatic chain and, if desired, having sufficient pendant aliphatic groups to render the molecule oil soluble with an amine or a hydrocarbyl polyamine, such as an ethylene amine, to give a mono or polycarboxylic acid amide. Preferred are those amides prepared from (1) a carboxylic acid of the formula $R^2COOH$, where $R^2$ is $C_{12-20}$ alkyl or a mixture of this acid with a polyisobutenyl carboxylic acid in which the polyisobutenyl group contains from 72 to 128 carbon atoms and (2) an ethylene amine, especially triethylene tetramine or tetraethylene pentamine or mixtures thereof.

Another class of useful nitrogen-containing compounds are hydrocarbyl monoamines and hydrocarbyl polyamines, e.g., those disclosed in U.S. Pat. No. 3,574,576, the contents of which are incorporated by reference herein. The hydrocarbyl group, which is preferably alkyl, or olefinic having one or two sites of unsaturation, usually contains from 9 to about 350 carbon atoms and preferably from about 20 to about 200 carbon atoms. Particularly preferred hydrocarbyl polyamines are those which are derived, e.g., by reacting polyisobutenyl chloride and a polyalkylene polyamine, such as an ethylene amine, e.g., ethylene diamine, diethylene triamine, tetraethylene pentamine, 2-aminoethylpiperazine, 1,3-propylene diamine, 1,2-propylenediamine, and the like.

Yet another class of useful nitrogen-containing compounds are the Mannich base compounds. These compounds are prepared from a phenol or $C_{9-200}$ alkylphenol, an aldehyde, such as formaldehyde or formaldehyde precursor such as paraformaldehyde, and an amine compound. The amine may be a mono or polyamine and typical compounds are prepared from an alkylamine, such as methylamine or an ethylene amine, such as, diethylene triamine, or tetraethylene pentamine, and the like. The phenolic material may be sulfurized and preferably is dodecylphenol or a $C_{80-100}$ alkylphenol. Typical Mannich bases which can be used in this invention are disclosed in U.S. Pat. Nos. 3,539,663, 3,649,229; 3,368,972 and 4,157,309, the contents of which are incorporated by reference herein.

Still yet another class of useful nitrogen-containing compounds are the phosphoramides and phosphonamides such as, for example, those disclosed in U.S. Pat. Nos. 3,909,430 and 3,968,157, the contents of which are incorporated by reference herein. These compounds may be prepared by forming a phosphorus compound having at least one P—N bond. They can be prepared, for example, by reacting phosphorus oxychloride with a hydrocarbyl diol in the presence of a monoamine or by reacting phosphorus oxychloride with a difunctional secondary amine and a monofunctional amine. Thiophosphoramides can be prepared by reacting an unsaturated hydrocarbon compound containing from 2 to 450 or more carbon atoms, such as polyethylene, polyisobutylene, polypropylene, ethylene, 1-hexene, 1,3-hexadiene, isobutylene, 4-methyl-1-pentene, and the like, with phosphorus pentasulfide and a nitrogen-containing compound as defined above, particularly an alkylamine, alkyldiamine, alkylpolyamine, or an alkyleneamine, such as ethylene diamine, diethylenetriamine, triethylenetetramine, tetraethylenepentamine, and the like.

Another class of useful nitrogen-containing compounds includes the so-called dispersant viscosity index improvers (VI improvers). These VI improvers are commonly prepared by functionalizing a hydrocarbon polymer, especially a polymer derived from ethylene and/or propylene, optionally containing additional units derived from one or more co-monomers such as alicyclic or aliphatic olefins or diolefins.

If desired, prior to dispensing the at least one base oil and at least one lubricating oil additive to provide the compositions herein, as discussed hereinbelow, it can be advantageous to conduct molecular modeling of proposed compounds for use in the compositions (i.e., formulations) to determine which compounds may provide potential leading candidate compositions. For example, calculations can be carried out involving such factors as, for example, transition states, bond lengths, bond angles, dipole moment, hydrophobicity, etc, of the compounds. This can be carried out using known software such as, for example, Quantum Mechanics available from Accelrys (San Diego, Calif.).

Software for the design of test libraries can be used to design the original compound test libraries based on input from the foregoing experimental program(s). This software can be used to efficiently design test libraries that cover the desired experimental space and utilize statistical experimental design methods. Other software can then be used to analyze the data from the experiments and correlate that data with the structure of the compounds and/or compound treatment conditions and/or reaction conditions. Such correlations are often referred to as QSAR software (Quantitative Structure Activity Relations) available from Accelrys (San Diego, Calif.). Such QSAR programs can then be used by the software to design subsequent compound test libraries for further screening.

The use of such QSAR programs can add to the efficiency of screening. As more data is collected, these QSAR programs can become more efficient at developing compounds libraries with increased probability for finding desirable compounds. For example, the compounds analyzed can be formulated into various lubricating oil compositions, as decribed hereinbelow, and then further analyzed by way of, for example, regression and analysis technologies, using known software, e.g., $C^2$-QSAR available from Accelrys (San Diego, Calif.). In this manner, validation of the data obtained from the molecular modeling can be achieved and then this data can also be stored in a data collector. In this way, new compounds, conceived by one skilled in the art can be checked by the QSAR software to predict their activity prior to their actual synthesis. Additionally, such software tools may be utilized to prioritize a list of possible compounds being considered for synthesis in such a way that one skilled in the art will have a higher probability for success.

Referring now to FIG. 1, an example of a system to provide the foregoing compositions in the plurality of respective test receptacles is generally illustrated as system 100. Representative of this system and method for providing the foregoing compositions in the plurality of respective test receptacles is one disclosed in co-pending U.S. patent application Ser. No. 10/699,510, filed on Oct. 31, 2003 and entitled "HIGH THROUGHPUT PREPARATION OF LUBRICATING OIL COMPOSITIONS FOR COMBINATORIAL LIBRARIES" by Wollenberg et al. and having a common assignee with the present application, the contents of which are incorporated by reference herein. It is to be understood that the present invention is not limited to this system and that other systems can be envisioned for providing the foregoing compositions in the plurality of respective test receptacles.

Generally, vessel 110 contains a supply of the foregoing base oils of lubricating viscosity B. Vessel 120 contains a supply of additive A, which can be any of the foregoing additives useful for modifying the properties of the base oil. As one skilled in the art would readily appreciate, one or more of vessels 110 and vessels 120 can be used when dispensing more than one base oil and/or more than one additive, respectively.

Tubular line 111 is a conduit for communicating the base oil B to nozzle portion 113, from which it can be dispensed into a selected test reservoir, as described below. The amount of base oil dispensed is determined by metering pump 112, which can be computer controlled.

Tubular line 121 is a conduit for communicating the lubricating oil additive A to nozzle portion 123, from which it can be dispensed into a selected test reservoir, as described below. The amount of lubricating oil additive dispensed is determined by metering pump 122, which also can be computer controlled. Computer programs and systems for automatically metering predetermined amounts of materials in accordance with a preselected protocol are known in the art and can be used herein.

Nozzles 113 and 123 are preferably in close proximity so that base oil B and additive A can be simultaneously dispensed in a test reservoir. Alternatively, base oil B and additive A can be sequentially added to the test reservoir. The nozzles 113 and 123 can comprise a multichannel pipette or one or more syringe needles.

The vessels 110 and 120 can be under pressure. Optionally, more than two vessels can be employed. Metering pumps suitable for use in the invention are known and commercially available. In the event that highly viscous lubricant base stock or additives are used, the vessels 110 and 120 and/or the tubular lines 111 and 121, metering pumps 112 and 122, and/or nozzles 113 and 123 can be heated to facilitate fluid flow therethrough.

The test frame 130 includes a block 131 of transparent material (e.g., glass) having a plurality of recesses 132 for receiving the dispensed additives or base oil and additives. The recesses provide test reservoirs wherein each reservoir contains lubricating oil additive compositions or lubricating oil compositions of a different and predetermined composition, i.e., the percentage and/or type of base oil and/or additives in each composition will vary from one reservoir to another. Optionally, the reservoirs can be individual receptacles (e.g., test tubes) mounted upon a rack, instead of being recesses in a block. Preferably, the test receptacles comprise transparent glass tubes. While five reservoirs, i.e., recesses 132a, 132b, 132c, 132d, 132e, are illustrated in FIG. 1, any number of reservoirs can be employed herein. For example the system can employ 20, 50, 100 or even more test receptacles and samples as required.

The individual reservoirs are adapted to hold relatively small amounts of lubricating oil samples. The sample size in each reservoir can generally be less than about 50 ml, preferably no more than about 20 ml, preferably no more than about 15 ml, more preferably no more than about 10 ml and yet more preferably no more than about 5 ml.

The test frame 130 and dispensing nozzles 113 and 123 are movable relative to one another. Although manual movement of the apparatus by an equipment operator is within the purview of the invention, robotic mechanisms with programmable movement are preferred. In one embodiment the test frame 130 is mounted upon a slidable carriage movable in a lateral and/or vertical direction so as to sequentially position a selected recess under the dispensing nozzles 113 and 123. In another embodiment, the nozzles 113 and 123, and optionally the vessels 110 and 120, are slidably movable laterally and/or vertically to accomplish positioning of the nozzles 113 and 123.

In a testing procedure, vessels 110 and 120 are filled with the selected lubricant base oil and additive(s), respectively. The apparatus of system 100 is moved such that dispensing nozzles 113 and 123 are positioned above and in alignment with recess 132a. A metered amount of base oil B and a metered amount of additive A are simultaneously dispensed into recess 132a. The dispensing nozzles 113 and 123 are thereafter repositioned to be in alignment with the next recess 132b and the metered amounts of additive A and/or base oil B are changed in accordance with a predetermined schedule of variation such that the lubricating oil in recess 132b has a different percentage composition of additive than that in recess 132a. The pattern is repeated as the nozzles 113 and 123 are sequentially aligned with the successive recesses 132c, 132d, and 132e so that each recess has a predetermined composition of lubricating oil.

The components A and B are preferably combined in the reservoirs by mixing, for example, by agitation of the frame 131, static mixing, individual stirring of the contents of the reservoirs (mechanical or magnetic stirring) and/or by bubbling the reservoir with gas, e.g., nitrogen. Optionally, base oil B and additive(s) A can be combined prior to dispensing into the respective reservoirs. For example, a single dispensing nozzle having a mixing chamber can be used, wherein base oil B and additive(s) A are metered into the mixing chamber and then dispensed through the nozzle into the reservoir.

Figure 2:
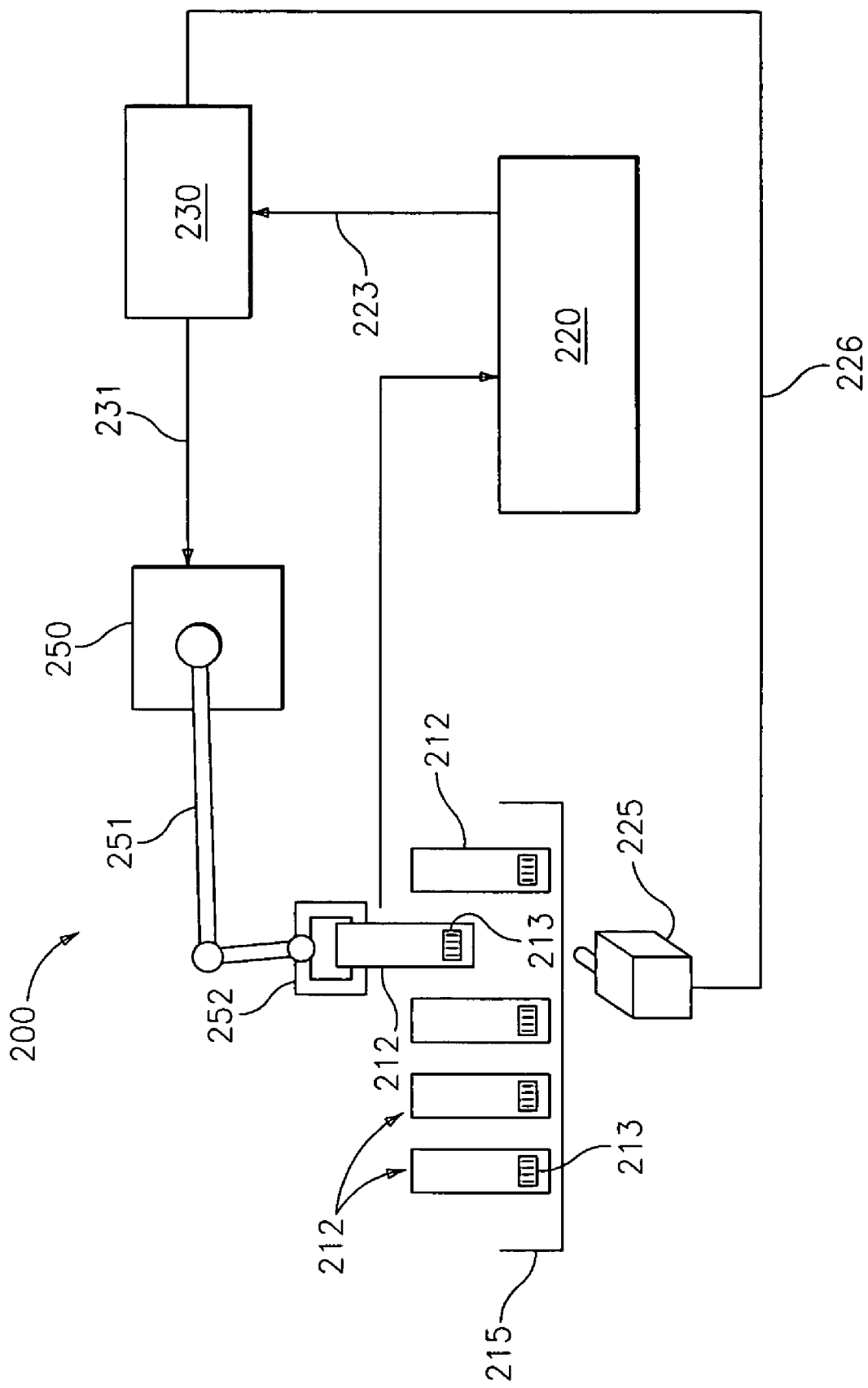
FIG. 2 is a schematic diagram of a system for measuring deposit formation tendencies of a plurality of samples of lubricating oil compositions.

Once the plurality of receptacles have been provided containing the lubricating oil compositions, the plurality of fluid samples can then be analyzed for deposit forming tendencies. Referring now to FIG. 2, a system for sequentially analyzing a plurality of fluid samples for deposit formation is schematically illustrated. System 200 is schematically illustrated wherein an array of test receptacles 212 are mounted in a holder 215. The system 200 is adapted to accommodate any number of test receptacles 212 (and samples). Each sample is identifiable, for example, by the position of its test receptacle in an ordered array in holder 215, or more preferably by having an identifying mark associated with it. For example, each test receptacle 212 can include an identifying bar code 213 affixed to the outer surface thereof. A bar code reader 225 is positioned so as to be able to read the individual bar codes of the respective test receptacles 212 and to transmit a bar code data signal to a computer controller 230 via a data transmission line 226 to electronically identify the sample. The bar code reader 225 is preferably movable with respect to the holder 215 in response to a signal from computer controller 230 so as to be positionable in alignment with selected individual test receptacles 212.

A robotic assembly 250 includes a movable arm 251 with a grasping mechanism 252. The robotic assembly is adapted to grasp an individual test receptacle 212 in accordance with selection instructions from computer controller 230 and move the test receptacle to a position in testing station 220 so that the sample in the receptacle can be measured for deposit formation data. The computer controller 230 is operatively associated with controls to the robotic assembly via control signal transmission line 231 to selectively retrieve predetermined test receptacles for measurement and then replace them in their assigned respective positions in the holder 215.

Testing station 220 includes means for testing the samples for deposit formation. Deposit formation data results of the test are converted to an electrical or optical signal and transmitted via signal transmission line 223 to computer controller 230. Various means for deposit formation testing are known and generally include subjecting the sample to a deposit formation environment and measuring the deposit formation of the sample over a predetermined period of time.

For example, in one test method for use herein a sample is weighed into a suitable testing apparatus, an instrument suitable for measuring deposit formation, e.g., a transparent substrate such a glass tube or rod, is at least partially inserted into the sample in the apparatus, and the sample is heated to a suitable temperature, e.g., a temperature ranging from about 150° C. to about 400° C. and preferably from about 200° C. to about 350° C., for a sufficient period of time for the sample to undergo oxidation, a time period ranging from about 8 hours to about 48 hours. After the predetermined period of time, the transparent tube is removed from the test apparatus, rinsed with a suitable solvent such as pentane and the amount of deposits is measured in accordance with the darkness of the deposit on the tube, the darkness indicating the quantity of the deposit and the amount of oxidation. The measurement is compared against a predetermined standard set of tubes. If desired, a liquid catalyst may be added to the sample to assist in accelerating oxidation and is chosen to simulate the types of metal ions typically found in an internal combustion engine.

To determine the deposit formation, a light source and a photocell can be employed. The amount of deposit can be measured by directing a beam of light from the light source through the tube and measuring the amount of light transmitted through the tube by means of the photocell. The opacity of the tube indicates the amount of deposit, and hence, the amount of oxidation of the sample.

Figure 3:
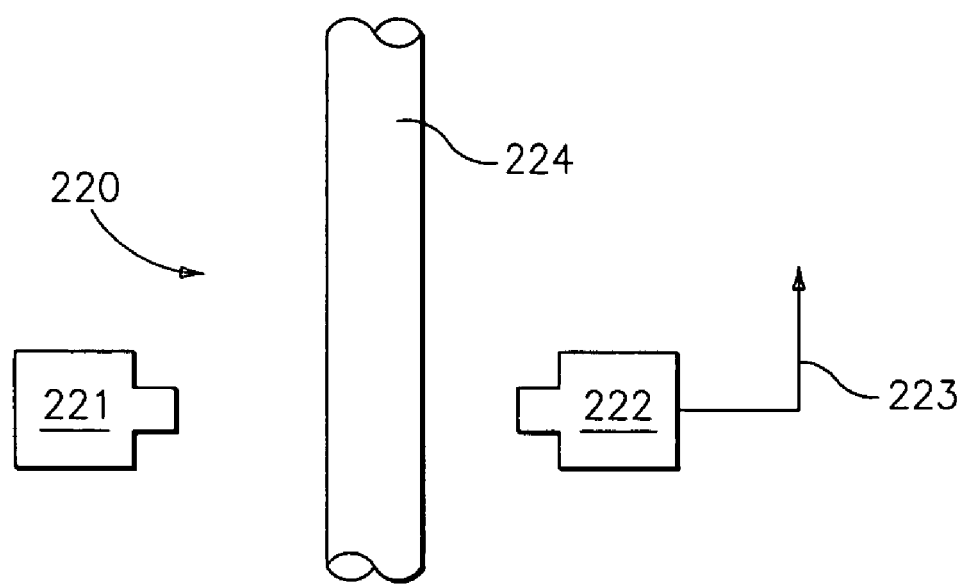
FIG. 3 is a schematic diagram of a photocell system for measuring deposit formation on a substrate.

For example, referring to FIG. 3, test tube 224 from the testing apparatus is positioned between light source 221 and photocell 222. A beam of light from the light source is directed through the test tube 224 and is measured by the photocell 222, which measures the amount of transmitted light, converts this reading to an electrical signal, and transmits the signal via line 223 to the computer controller 230. The computer controller 230 has stored values of light transmittance (or opacity) for the standard set of tubes and rates the deposit formation of the test sample by comparison with the standard set. The deposit formation rating is assigned to the test sample (which can be identified by the bar code) and the information is stored as a component of the data library. The computer controller can thereafter modify the selection instructions. Programming to accomplish the various functions of the computer controller 230 are within the purview of those with skill in the art.

In an alternative embodiment of the method of the present invention, a sample is placed in a transparent testing apparatus, e.g., a glass petri dish, and heated to a predetermined temperature, e.g., 150° C. to about 400° C. and preferably from about 200° C. to about 350° C., using, for example, a hot plate, for a predetermined period time. The predetermined period of time can vary widely and can range from about 8 hours to about 48 hours and preferably from about 10 hours to about 18 hours. After the predetermined period of time, the transparent testing apparatus is washed with a light hydrocarbon solvent, e.g., pentane, to remove any soluble lubricating oil to leave any remaining oxidized deposits on the testing apparatus. Then, the transparent testing apparatus containing any deposits is measured utilizing, for example, an analytical balance, and the measurement is compared against a predetermined weight of the transparent testing apparatus to determine the weight of the deposits. The data is then recorded in a database.

Figure 4:
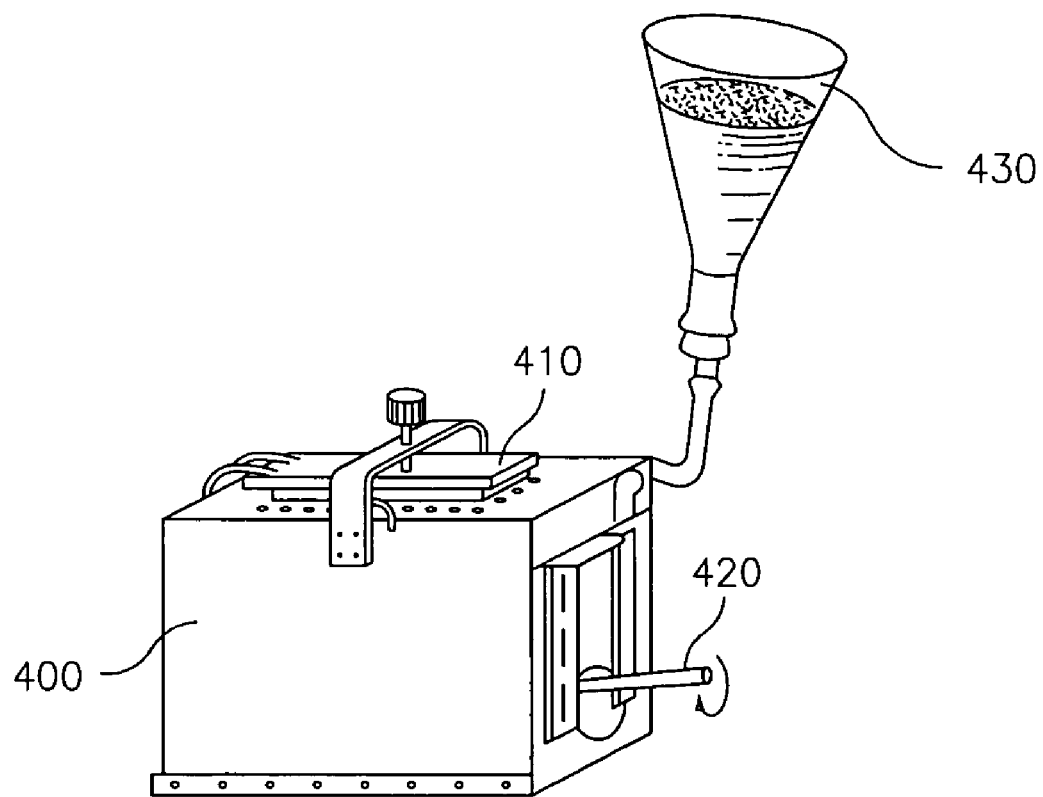
FIG. 4 is a schematic diagram of a system for measuring deposit formation tendencies of a plurality of samples of lubricating oil compositions employing a panel coker testing method.

In another deposit formation test method of the present invention (known as the coking tendency test of finished oil—Federal Test Method Standard 3462-791A (panel coker test method)), each of the foregoing samples can be placed in a chamber suitable to determine deposit formation. Referring now to FIG. 4, chamber 400 can be, for example, a stainless steel chamber, wherein one side of the chamber has an opening therein and a testing panel 410 suitable for measuring deposit formation, e.g., aluminum, is operatively connected to the chamber over the opening such that the side of the material facing the chamber is exposed in the opening. A shaft 420 is operatively connected to chamber 400 and contains, for example, bristles at the end of the shaft located in chamber 400. Additionally, a reservoir 430 for holding the composition sample to be tested can be connected to chamber 400 with a tube for metering the sample into chamber 400 together with a system for recirculating the sample back into reservoir 430 (not shown). Alternatively, a reservoir for holding the sample can be in chamber 400 and below shaft 420 such that the bristles of shaft 420 are in contact with the sample (not shown).

In use, testing panel 410 and the sample are maintained at a predetermined temperature, e.g., from about 100° C. to about 400° C. and preferably from about 175° C. to about 275° C. for panel 410 and from about 80° C. to about 250° C. and preferably from about 160° C. to about 200° C. for the sample, shaft 420 is rotated by applying a predetermined power and the sample is metered into chamber 400 and contacted with the bristles of rotating shaft 420 such that the sample is sprayed onto the heated testing panel 410 for a predetermined period of time. The predetermined period of time can vary widely, e.g., from about 1 hour to 75 hours and preferably from about 24 hours to about 50 hours. If desired, air or other typical combustion atmospheres (e.g., $NO_x$) can be blown into the chamber at a constant rate of flow to maintain the chamber at normal atmospheric conditions. The air flow rate can be determined by one skilled in the art.

After the predetermined period of time, the testing panel is removed from the chamber, optionally rinsed with a suitable solvent such as pentane or petroleum ether and allowed to dry for a predetermined period of time. The amount of deposits can then be measured by a suitable measuring device, e.g., an analytical balance, by comparing the weight of the panel containing deposits to the predetermined weight of the panel by itself. The data is then recorded in a database.

In another embodiment of the present invention, a method to determine the deposit formation on, for example, a transparent tube, is used (e.g., Komatsu Hot Tube test). In this method, a transparent glass tube can be placed inside a metal heating block, e.g., an aluminum heating block, and a small air hose is attached to a holder at the bottom of the glass tube. Next, a suitable nozzle, e.g., about a 5 ml syringe, and a suitable hose, e.g., about a 12 inch flexible tubing, are filled with the oil sample.

The tubing is attached to a holder on the glass tube above the air hose and oil is steadily introduced into the glass tube by the nozzle. Air forces the test oil up the glass tube through the heating block for the duration of the test. The rate of air flow and sample introduction are controlled such that the entire sample is injected within a predetermined time, e.g., a 16 hour time period. The oxidation of the oil gradually forms a dark deposit on the inner wall of the glass tube. The heating block is temperature controlled within small limits and the test conditions are generally chosen over a range of temperatures, e.g., from about 230° C. to about 330° C., and tests can be run at different temperatures to determine deposit formation over a temperature range. After a predetermined period of time (e.g., 16 hours) the glass tube is removed from the test apparatus, rinsed with a suitable solvent, and the amount of deposit is measured in accordance with the darkness of the deposit in the tube, the darkness indicating the quantity of the deposit and the amount of oxidation. The measurement is compared against a predetermined standard set of tubes.

Figure 5:
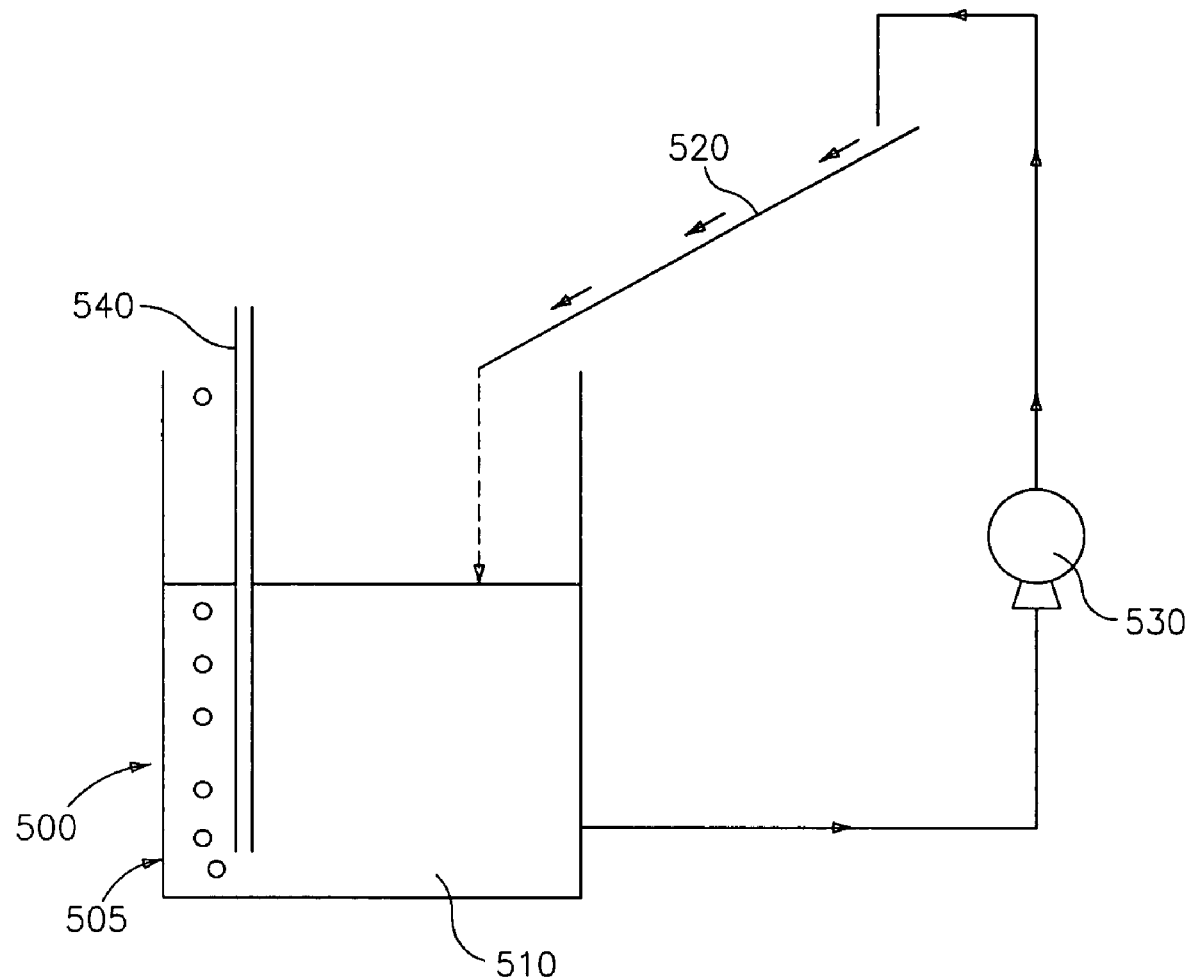
FIG. 5 is a schematic diagram of a system for measuring deposit formation tendencies of a plurality of samples of lubricating oil compositions employing a Wolf Strip Test method.

Another embodiment of the present invention utilizes the Wolf Strip Test such as, for example, DIN 51392. Referring to FIG. 5, system 500 advantageously configures sample 510 to circulated from vessel 505, over substrate 520 heated to a predetermined temperature, e.g., from about 100° C. to about 400° C. and preferably from about 200° C. to about 300° C., and back into vessel 500. Sample 510 can be circulated by conventional techniques using, for example, micropump 530. Additionally, air is bubbled into vessel 500 at a constant rate of flow, e.g., about 25 ml/h to about 75 ml/h, using tube 540. After a predetermined period of time, e.g., from about 8 hours to about 24 hours and preferably from about 10 hours to about 18 hours, the testing substrate is removed from the chamber, rinsed with a suitable solvent such as pentane or petroleum ether and the amount of deposits can then be measured by a suitable measuring device, e.g., an analytical balance, by comparing the weight of the panel containing deposits to the predetermined weight of the panel by itself. The data is then recorded in a database.

Another embodiment of the present invention can be shown in FIG. 6A where system 600 contains at least substrate 610, e.g., a glass substrate, having a recess in at least a portion therein and placed on heating blocks 620 A and 620 B. Heating block 620A is heated to a first predetermined temperature, e.g., about 200° C. to about 300° C., and heating block 620 B is heated to a second predetermined temperature, about 300° C. to about 400° C., with the temperature of heating block 620 B being higher than the temperature of heating block 620 A. Preferably, heating blocks 620 A and 620 B are configured such that substrate 610 is placed on an incline, e.g., about 45 to 90°, to determine deposit formation (see FIG. 6B). A sample is placed at the top end of the recess 630 in substrate 610 placed on heating block 620 A and allowed to flow down the recess towards heating block 620 B. Deposit formation data can then be gathered by determining at which temperature deposit formation occurs for the different samples by making a linear extrapolation of temperature based on the distance between the two temperature points. The data is then recorded in a database.

If desired, an assigned value of deposit formation is programmed into the computer controller for "pass/fail" determination. Assigned pass/fail values can be selected based upon performance requirements for specific lubricant applications or fuel applications and prospective operating environments. If the test sample fails by having an excessively high deposit formation value, the test sample can be electronically marked and future testing of lubricant oil formulations having the same composition as the sample can be eliminated from further testing for other performance characteristics. By not retesting failed samples the system can be made to operate more efficiently, energy and time being spent only on samples which prospectively meet the desired product specifications.

If desired, the results of the method of the present invention can be monitored from a remote location, i.e., a location which is not in direct or at least in visual contact with the system operating the method of the invention. A remote location can be, for example, a central process control system or room which, as part of the overall system for use herein, monitors and controls the system as well as records the outputs of each of the results of the tests being carried out. In this way, it becomes possible for less interaction with personnel being stationed at the location of the system. Suitable data lines, with which the results of the output, as well as control commands, may be transmitted, are known.

Deposit formation data regarding each of the compositions described herein can be stored in a relational database to provide a combinatorial lubricating oil composition library. Alternatively, the system may be electrically connected to a signal data collector comprising a computer microprocessor for system operation and control to collect the data from the various tests over an extended period of time to compile the combinatorial lubricating oil composition library. The database can be used to find optimum combinations for a desired product stream, and can be particularly useful when the desired product stream varies depending on market factors. When the product requirements change, appropriate combinations can be selected to prepare the desired product.

Relational database software can be used to correlate the identity of the lubricating oil compositions to the analytical deposit formation data obtained therefrom. Numerous commercially available relational database software programs are available, for example, from Oracle, Tripos, MDL, Oxford Molecular ("Chemical Design"), IDBS ("Activity Base"), and other software vendors.

Relational database software is a preferred type of software for managing the data obtained during the methods described herein. However, any software that is able to create a "memory map" of each of the compositions described herein and correlate that information with the information obtained from the deposit formation measurements can be used. This type of software is well known to those of skill in the art.

While the above description contains many specifics, these specifics should not be construed as limitations of the invention, but merely as exemplifications of preferred embodiments thereof. For example, deposit formation tendency tests other than those described herein can be used to provide deposit formation data for the plurality of different lubricating oil composition samples tested. Those skilled in the art will envision many other embodiments within the scope and spirit of the invention as defined by the claims appended hereto.

What is claimed is:

1. A high throughput method for screening lubricating oil composition samples, under program control, comprising the steps of:

(a) providing a plurality of different lubricating oil composition samples, each sample comprising (i) a major amount of at least one base oil of lubricating viscosity, and (ii) a minor amount of at least one lubricating oil additive;

(b) measuring deposit formation of each sample comprising heating a substrate to a first predetermined temperature and the sample to a second predetermined temperature, contacting the substrate with the sample and determining the amount of deposits formed on the substrate after a predetermined period of time to provide deposit formation data for each sample; and, (c) outputting the results of step (b).

2. The method of claim 1, wherein the base oil is a natural or synthetic oil.

3. The method of claim 1, wherein the at least one lubricating oil additive is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

4. The method of claim 1, wherein the at least one lubricating oil additive is selected from the group consisting of antioxidants, detergents, ashless dispersants and mixtures thereof.

5. The method of claim 1, wherein the substrate is a transparent material.

6. The method of claim 5, wherein the step of determining the amount of deposits formed on the transparent substrate comprises determining the opacity or light scattering of the sample and comparing the determined opacity or light scattering with the opacity or light scattering of a reference sample.

7. The method of claim 6, wherein the opacity of the sample is determined by measuring the intensity of light passed through a sample.

8. The method of claim 6, wherein the plurality of samples are in a linear array and are sequentially moved to a measuring station between a light source and a photocell for individually measuring the deposit formation of each sample.

9. The method of claim 1, wherein the substrate is aluminum.

10. The method of claim 1, wherein the first predetermined temperature is about 100° C. to about 400° C. and the second predetermined temperature is about 80° C. to about 250° C.

11. The method of claim 1, wherein a robotic assembly selectively retrieves the samples from an array of samples and individually positions the samples in a testing station for determination of the deposit formation.

12. The method of claim 11, wherein said robotic assembly is controlled by a computer.

13. The method of claim 1, wherein the step of outputting comprises storing the results of step (b) on a data carrier.

14. The method of claim 1, further comprising the step of using the result of step (c) as a basis for obtaining a result of further calculations.

15. The method of claim 1, wherein the at least one lubricating oil additive further comprises a diluent oil to form an additive concentrate.

16. The method of claim 1, wherein the lubricating oil composition samples have a volume of no more than about 50 ml.

17. The method of claim 1, wherein the lubricating oil composition samples have a volume of no more than about 20 ml.

18. The method of claim 1, wherein the lubricating oil composition samples have a volume of no more than about 15 ml.

19. The method of claim 1, wherein the lubricating oil composition samples have a volume of no more than about 10 ml.

20. A high throughput method for screening lubricating oil composition samples, under program control, comprising the steps of:

(a) providing a plurality of different lubricating oil composition samples, each sample comprising (i) a major amount of at least one base oil of lubricating viscosity, and (ii) a minor amount of at least one lubricating oil additive;

(b) measuring deposit formation of each sample comprising heating one end of a substrate to a first predetermined temperature and the opposite end of the substrate to a second predetermined temperature, wherein the first predetermined temperature is different than the second predetermined temperature; contacting the substrate with the sample and determining the temperature at which deposits formed on the substrate to provide deposit formation data for each sample; and, (c) outputting the results of step (b).

21. The process of claim 20, wherein the base oil of lubricating viscosity is a natural or synthetic oil.

22. The process of claim 20, wherein the at least one lubricating oil additive is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

23. The process of claim 20, wherein the at least one lubricating oil additive is selected from the group consisting of antioxidants, detergents, ashless dispersants and mixtures thereof.

* * * * *